United States Patent
Kang et al.

(10) Patent No.: US 10,816,868 B2
(45) Date of Patent: Oct. 27, 2020

(54) ACTIVE MOLECULE DELIVERY SYSTEM COMPRISING MICROCELLS

(71) Applicant: E Ink California, LLC, Fremont, CA (US)

(72) Inventors: Yih-Ming Kang, Fremont, CA (US); Donald A. Schultz, San Jose, CA (US); Lei Liu, Fremont, CA (US); Renfu Cheng, Fremont, CA (US); Lin Shao, Fremont, CA (US); Hui Du, Milpitas, CA (US); Ming Wang, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 232 days.

(21) Appl. No.: 16/100,528

(22) Filed: Aug. 10, 2018

(65) Prior Publication Data

US 2018/0348590 A1  Dec. 6, 2018

Related U.S. Application Data

(60) Continuation-in-part of application No. 15/238,075, filed on Aug. 16, 2016, now Pat. No. 10,073,318,
(Continued)

(51) Int. Cl.
*G09G 3/34* (2006.01)
*G02B 26/02* (2006.01)
(Continued)

(52) U.S. Cl.
CPC .......... *G02F 1/167* (2013.01); *A61M 31/002* (2013.01); *A61M 35/003* (2013.01); *B29C 39/00* (2013.01);
(Continued)

(58) Field of Classification Search
CPC ...... G02B 26/02; G02B 26/026; G02B 26/08; G09G 3/34; G09G 3/344; G09G 3/3446;
(Continued)

(56) References Cited

U.S. PATENT DOCUMENTS 5,384,649 A    1/1995 Takimoto
6,822,783 B2  11/2004 Matsuda
(Continued)

FOREIGN PATENT DOCUMENTS

JP    2011014068 A    1/2011
JP    2013033125 A    2/2013
(Continued)

OTHER PUBLICATIONS

Liang, R.C., "BreakThrough-Newly-Developed Color Electronic Paper Promises—Unbeatable Production Efficiency", Nikkei Microdevices, p. 3 (Dec. 2002). (in Japanese, with English translation).
(Continued)

*Primary Examiner* — Robert E. Tallman
(74) *Attorney, Agent, or Firm* — Ioannis Constantinides

(57) ABSTRACT

The present invention is directed to an active molecule delivery system comprising a plurality of microcells wherein each of the microcells has a bottom, the panel has a first area and a second area, and the microcells in the first area have substantially the same bottom thickness and the microcells in the second area have added bottom thicknesses. Such a panel is useful for many applications, such drug administrations.

12 Claims, 11 Drawing Sheets

Related U.S. Application Data which is a division of application No. 14/486,994, filed on Sep. 15, 2014, now Pat. No. 9,436,057, application No. 16/100,528, which is a continuation-in-part of application No. 15/933,442, filed on Mar. 23, 2018, now abandoned.

(60) Provisional application No. 61/881,346, filed on Sep. 23, 2013, provisional application No. 62/475,924, filed on Mar. 24, 2017.

(51) Int. Cl.

| | |
|---|---|
| *G09G 3/20* | (2006.01) |
| *G02F 1/167* | (2019.01) |
| *G02F 1/1343* | (2006.01) |
| *G02F 1/1681* | (2019.01) |
| *A61M 31/00* | (2006.01) |
| *B29C 39/00* | (2006.01) |
| *A61M 35/00* | (2006.01) |
| *G02F 1/1675* | (2019.01) |
| *G02F 1/1333* | (2006.01) |
| *G02F 1/1347* | (2006.01) |

(52) U.S. Cl.
CPC ..... *G02B 26/026* (2013.01); *G02F 1/134336* (2013.01); *G02F 1/1675* (2019.01); *G02F 1/1681* (2019.01); *G09G 3/344* (2013.01); *G02F 1/1333* (2013.01); *G02F 1/1347* (2013.01); *G09G 3/2003* (2013.01)

(58) Field of Classification Search
CPC .............. G09G 2310/06; G02F 1/1347; G02F 1/134336; G02F 1/167; G02F 1/1672
See application file for complete search history.

(56) References Cited

U.S. PATENT DOCUMENTS

| | | | |
|---|---|---|---|
| 6,831,770 B2 | 12/2004 | Liang | |
| 6,859,302 B2 | 2/2005 | Liang | |
| 6,870,662 B2 | 3/2005 | Tseng | |
| 6,930,818 B1 | 8/2005 | Liang | |
| 6,975,373 B2 | 12/2005 | Il | |
| 7,206,119 B2 | 4/2007 | Honeyman et al. | |
| 7,413,765 B2 | 8/2008 | Ito | |
| 7,417,787 B2 | 8/2008 | Chopra | |
| 7,713,836 B2 | 5/2010 | Aoki | |
| 7,715,088 B2* | 5/2010 | Liang | B29C 35/0888 359/296 |
| 7,880,958 B2 | 2/2011 | Zang | |
| 8,054,288 B2 | 11/2011 | Sugita | |
| 8,169,691 B1 | 5/2012 | Miyamoto | |
| 8,498,040 B2 | 7/2013 | Yi | |
| 8,542,430 B2 | 9/2013 | Yasui | |
| 8,570,271 B2 | 10/2013 | Lee | |
| 8,582,197 B2 | 11/2013 | Liang | |
| 8,995,046 B2 | 3/2015 | Mori | |
| 9,248,013 B2 | 2/2016 | Tai | |
| 9,388,307 B2 | 7/2016 | Li | |
| 9,436,057 B2 | 9/2016 | Kang | |
| 2007/0205979 A1 | 9/2007 | Bigelow | |
| 2011/0043543 A1 | 2/2011 | Chen | |
| 2011/0069001 A1 | 3/2011 | Lee | |
| 2011/0133627 A1* | 6/2011 | Yi | G02F 1/167 313/483 |
| 2016/0357084 A1 | 12/2016 | Kang | |
| 2018/0271800 A1 | 9/2018 | Liu | |

FOREIGN PATENT DOCUMENTS

| | | |
|---|---|---|
| JP | 2013164538 A | 8/2013 |
| KR | 20120076256 A | 7/2012 |

OTHER PUBLICATIONS

Liang, R.C. et al., "Microcup Electrophoretic Displays by Roll-to-Roll Manufacturing Processes", IDW '02, Paper EP2-2, pp. 1337-1340, (Dec. 2002).

Liang, R.C., "Microcup Electrophoretic and Liquid Crystal Displays by Roll-to-Roll Manufacturing Processes", Presented at Flexible Microelectronics & Displays Conference of U.S. Display Consortium, Phoenix, Arizona, USA (Feb. 2003).

Liang, R.C. et al., "Microcup LCD, A New Type of Dispersed LCD by a Roll-to-Roll Manufacturing Process", Presented at IDMC, Paper We-02-04, pp. 1-4, Taipei, Taiwan, (Feb. 2003).

Liang, R.C. et al., "Passive Matrix Microcup Electrophoretic Displays", IDMC'03, Paper FR-17-5, p. 1-4, Taipei, Taiwan, (Feb. 2003).

Liang, R.C.et al., "Microcup Displays: Electronic Paper by Roll-to-Roll Manufacturing Processes" Journal of the SID, 11(4), pp. 621-628, (Feb. 2003).

Chen, S.M., "Revolution electronic paper: The New Application and the Dynamics of Companies", Topology Research Institute, pp. 1-10, (May 2003). (in Chinese, English abstract attached).

Liang, R.C. et al., "Microcup Active and Passive Matrix Electrophoretic Displays by a Roll-to-Roll Manufacturing Processes", SID 03 Digest, Paper 20.1, pp. 838-841 (May 2003).

Lee, H. et al., "SiPix Microcup Electronic Paper—An Introduction" Advanced Display, Issue 37, pp. 4-9, (Jun. 2003). (in Chinese, English abstract attached).

Chen, S.M., "The Applications for the Revolutionary Electronic Paper Technology", OPTO News & Letters, 102, pp. 37-41 (Jul. 2003). (in Chinese, English abstract attached).

Zang, H.M. et al., "Microcup Electronic Paper by Roll-to-Roll Manufacturing Processes", The Spectrum, 16(2), pp. 16-21 (2003).

Allen, K, "Electrophoretics Fulfilled. Emerging Displays Review: Emerging Display Technologies, Monthly Report", Stanford Resources Display Insight, pp. 9-14 (Oct. 2003).

Kleper, M. et al., "An Investigation of the Emerging and Developing Technologies Related to the Generation Beyond Print-on-Paper", Advanced Display Technologies, Rochester Institute of Technology, pp. 13-15, (Oct. 2003).

Zang, H.M. "Microcup Electronic Paper by Roll-to-Roll Manufacturing Processes", Presentation at the Advisory Board Meeting, Bowling Green State Univ., Ohio, USA (Oct. 2003).

Chung, J. et al., "Microcup Electrophoretic Displays, Grayscale and Color Rendition", IDW, AMD2 & EP1-2, pp. 243-246 (Dec. 2003).

Ho, C. et al., "Microcup Electronic Paper by Roll-to-Roll Manufacturing Processes", Presentation conducted at FEG, Nei-Li, Taiwan, (Dec. 2003).

Zang, H.M. et al., "Threshold and Grayscale Stability of Microcup Electronic Paper", SPIE vol. 5289, pp. 102-108, (Jan. 2004).

Zang, H.M. "Microcup Electronic Paper", Presentation at the Displays & Microelectronics Conference of U.S. Display Consortium, Phoenix, Arizona, USA (Feb. 2004).

Wang, X. et al., "Microcup Electronic Paper and the Converting Processes", ASID, 10.1.2-26, pp. 396-399, Nanjing, China, (Feb. 2004).

Chaug, Y.S. et al., "Roll-to-Roll Processes for the Manufacturing of Patterned Conductive Electrodes on Flexible Substrates", Mat Res. Soc. Symp. Proc., vol. 814, I9.6.1., (Apr. 2004).

Liang, R.C., "Microcup Electronic Paper by Roll-to-Roll Manufacturing Process", Presented at the Flexible Displays & Electronics 2004 of Intertech, San Fransisco, California, USA, (Apr. 2004).

Hou, J. et al., "Reliability and Performance of Flexible Electrophoretic Displays by Roll-to-Roll Manufacturing Processes", SID Digest, 32.3, pp. 1066-1069 (May 2004).

Wang, X. et al., "Microcup Electronic Paper and the Converting Processes", Advanced Display, Issue 43, pp. 48-51 (Jun. 2004). (in Chinese, with English abstract).

Liang, R.C. et al., "Format Flexible Microcup Electronic Paper by Roll-to-Roll Manufacturing Process", Presented at 14th FPD Manufacturing Technology Expo & Conference, Tokyo, Japan, (Jun. 30, 2004-Jul. 2, 2004).

(56) References Cited

OTHER PUBLICATIONS

Liang, R.C., "Flexible and Rollable Displays/Electronic Paper—Technology Overview", Presented at the METS conference, Taipei, Taiwan, (Oct. 2004).
Bardsley, J.N. et al., "Microcup Electrophoretic Displays", USDC Flexible Display Report, 3.1.2. pp. 3-12 to 3-16, (Nov. 2004).
Ho, Candice, "Microcup Electronic Paper Device and Application", Presentation conducted at USDC 4th Annual Flexible Display and Microelectronics Conference, Phoenix, Arizona, USA, (Feb. 1, 2005).
Zang, H.M. et al., "Flexible Microcup EPD by RTR Process", Presentation conducted at 2nd Annual Paper-Like Displays Conference, St. Pete Beach, Florida, USA, (Feb. 9-11, 2005).
Liang, R.C., "Flexible and Roll-able Displays/Electronic Paper—A Brief Technology Overview", Presentation at Flexible Display Forum, Taiwan (Feb. 2005).
Wang, X. et al., "Inkjet Fabrication of Multi-Color Microcup Electrophorectic Display", 5th Flexible Microelectronics & Displays Conference of U.S. Display Consortium, Phoenix, AZ, USA, (Feb. 2006).
Zang, H.M., et al., "Monochrome and Area Color Microcup EPDs by Roll-to-Roll Manufacturing Processes", ICIS 06 International Congress of Imaging Science Final Program and Proceedings, pp. 362-365, Rochester, New York, USA (May 2006).
Wang, X. et al., "Roll-to-Roll Manufacturing Process for Full Color Electrophoretic Film", SID 06 Digest, vol. 37, Issue 1, pp. 1587-1589, (Jun. 2006).
Zang, H.M., "Monochrome and Area Color Microcup EPDs by Roll-to-Roll Manufacturing Process", Presentation conducted at the Fourth Organic Electronics Conference and Exhibition (OEC-06), Frankfurt, Germany, (Sep. 25-27, 2006).
Ho, Andrew, "Embedding e-Paper in Smart Cards, Pricing Labels & Indicators", Presentation conducted at Smart Paper Conference, Atlanta, GA, USA (Nov. 15-16, 2006).
Zang, H.M. "Developments in Microcup Flexible Displays", Presentation conducted at the 6th Annual Flexible Display and Microelectronics Conference, Phoenix, AZ, Feb. 6-8, 2007.
Zang, H.M. et al., "Microcup e-Paper for Embedded and Flexible Designs", IDMC'07, Taipei International Convention Center, Taiwan, (Jul. 2007).
Sprague, R.A., "SiPix Microcup Electrophoretic Epaper for Ebooks", NIP 25, 2009, pp. 460-462; (Sep. 23, 2009). (Presentation conducted on Sep. 23, 2009 at the 25th Int'l Conference on Digital Printing Technologies,Louisville, Kentucky, USA.).
Korean Intellectual Property Office, PCT/US2014/055575, International Search Report and Written Opinion, dated Dec. 23, 2014.
European Patent Office; EP Appl. No. 14846369.8; Extended European Search Report; dated May 8, 2017.
Korean Intellectual Property Office, PCT/US2019/034853, International Search Report and Written Opinion, dated Sep. 25, 2019. dated Sep. 25, 2019.

\* cited by examiner

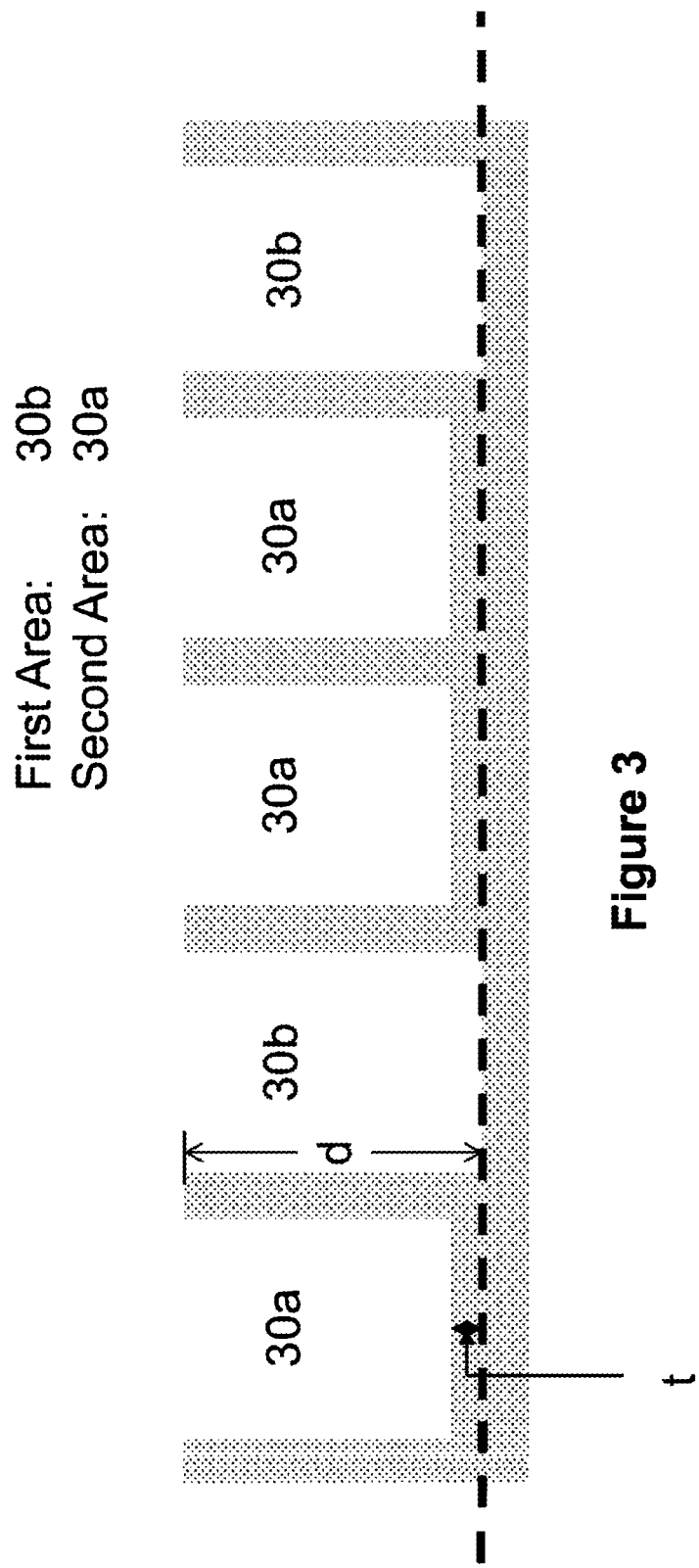

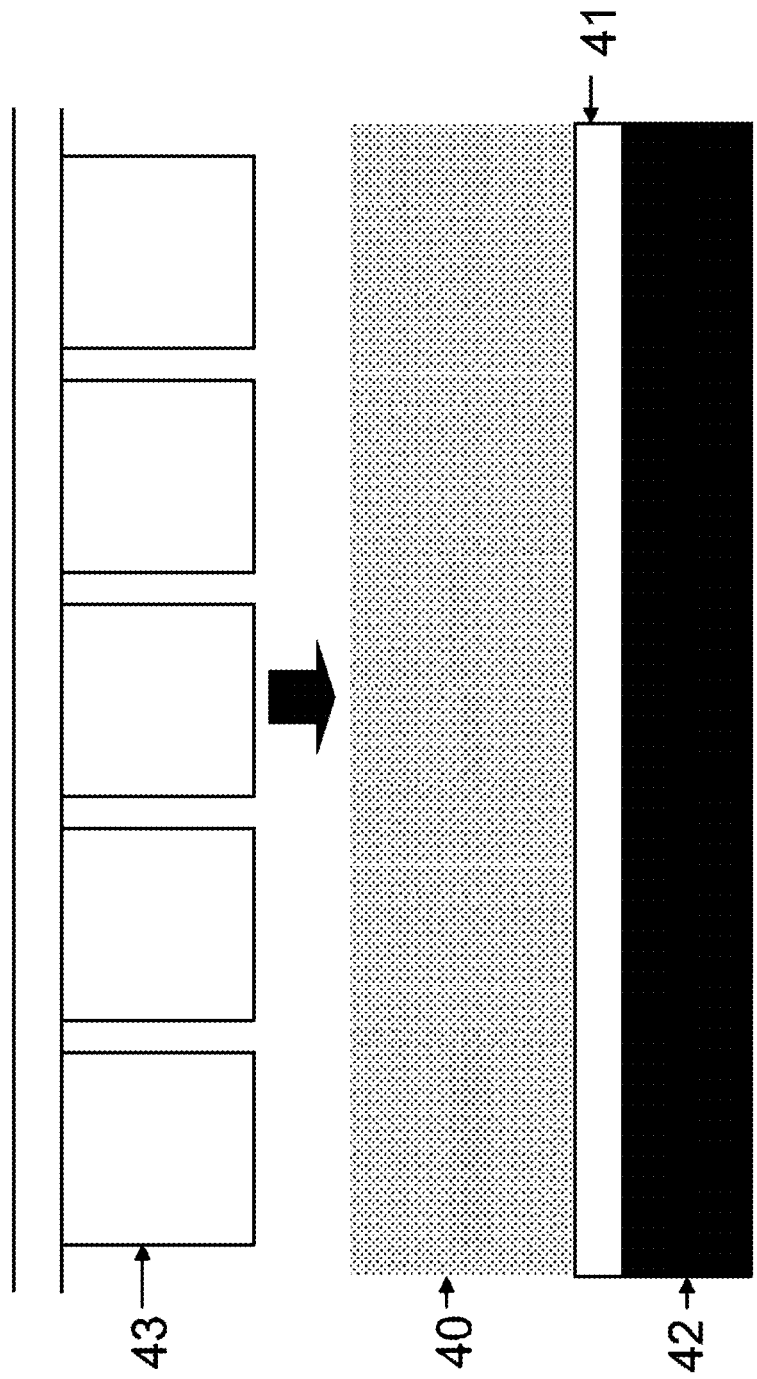

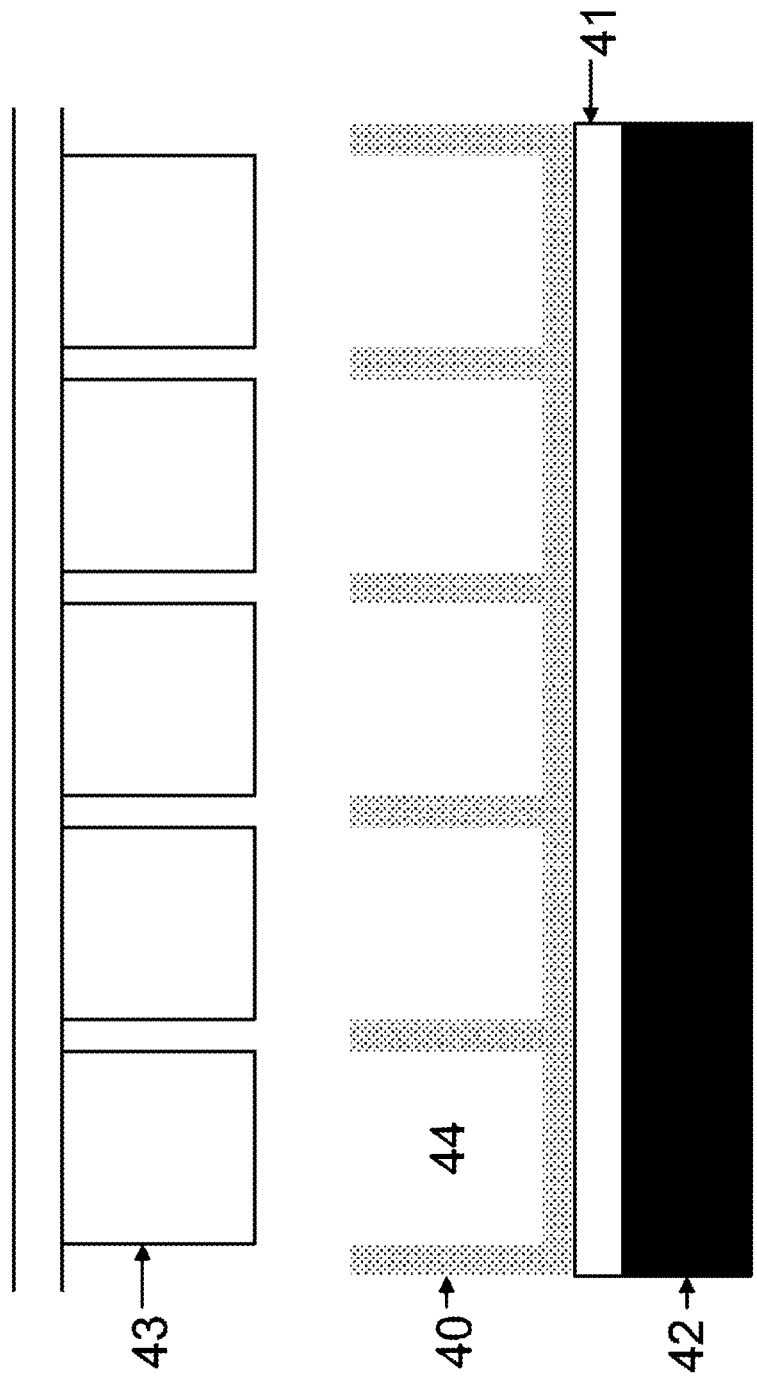

ACTIVE MOLECULE DELIVERY SYSTEM COMPRISING MICROCELLS

This application claims benefit of application Ser. No. 14/486,994, filed on Sep. 15, 2014, and application Ser. No. 15/933,442, filed on Mar. 23, 2018, where the U.S. Ser. No. 14/486,994 application is based on and claims priority to U.S. Provisional Application No. 61/881,346, filed Sep. 23, 2013, and the U.S. Ser. No. 15/933,442 application is based on and claims priority to U.S. Provisional Application No. 62/475,924, filed Mar. 24, 2017.

The entire contents of the aforementioned applications are herein incorporated herein by reference.

FIELD OF THE INVENTION

The present invention is directed to an active delivery system.

SUMMARY OF THE INVENTION

The present invention is directed to an active molecule delivery system which comprises microcells filled with an electrophoretic fluid wherein each of the microcells has a bottom and one surface of the bottom is in contact with the electrophoretic fluid, the display panel has a first area and a second area, and the microcells in the first area have substantially the same bottom thickness and the microcells in the second area have added bottom thicknesses.

In one embodiment, the microcells in the second area have a bottom thickness which is 0.001 micron to 9/10 of the depth of the microcells in the first area, more than the bottom thickness of the microcells in the first area.

In one embodiment, the microcells in the second area have a bottom thickness which is 0.001 micron to ½ of the depth of the microcells in the first area, more than the bottom thickness of the microcells in the first area.

In one embodiment, the bottom thicknesses of the microcells in the second area are not the same.

In one embodiment, an electrophoretic fluid filled in the microcells in both the first and second areas comprises one type of charged particles dispersed in a solvent or solvent mixture. In another embodiment, an electrophoretic fluid filled in the microcells in the first and second areas comprises two types of charged particles dispersed in a solvent or solvent mixture. In a further embodiment, an electrophoretic fluid filled in the microcells in the first and second areas comprises more than two types of charged particles dispersed in a solvent or solvent mixture.

In one embodiment, the active molecule delivery system is sandwiched between two electrode layers. In one embodiment, the two electrode layers are non-patterned conductive layers. In another embodiment, one of the electrode layers is a common electrode layer and the other electrode layer is a thin-film-transistor matrix driving system or segmented backplane driving system.

In one embodiment, the display panel is used in bar codes, anti-counterfeiting labels, direction signage or shelf labels. In another embodiment, the display panel is used in a watermark application.

Another aspect of the present invention is directed to a method for the preparation of an active molecule delivery system of the present invention, which comprises:

a) providing a nip roller on the surface of which has carved-out areas to form a pattern which pattern is a positive or negative image of an intended pattern for the display panel;

b) coating an embossable composition over a substrate layer which is on the surface of the nip roller; and c) applying a male mold over the embossable composition.

In one embodiment, the carved-out areas have different depths.

In one embodiment, the substrate layer is attached to an electrode layer.

A further aspect of the present invention is directed to a method for the preparation of an active molecule delivery system of the present invention, which comprises:

a) providing microcells;

b) filling the microcells in a pre-determined area, with a chemical composition in a solvent;

c) removing the solvent; and d) optionally curing the chemical composition after removal of the solvent.

In one embodiment, the solvent is methyl ethyl ketone, acetone, or isopropyl alcohol. In one embodiment, the microcells are filled with different concentrations of chemical compositions. In one embodiment, the concentrations are in the range of 0.01% to 90% by weight. In one embodiment, the concentrations are in the range of 0.01% to 50% by weight.

In one embodiment, the chemical composition is not the same as a composition from which the microcells are formed. In another embodiment, the chemical composition is the same as a composition from which the microcells are formed.

BRIEF DISCUSSION OF THE DRAWINGS

FIG. 3 illustrates a display panel of the present invention in which microcells in one area have thicker bottom than microcells in another area.

FIGS. 4A and 4B illustrate an embossing process for preparing the microcells.

DETAILED DESCRIPTION OF THE INVENTION

Figure 1:
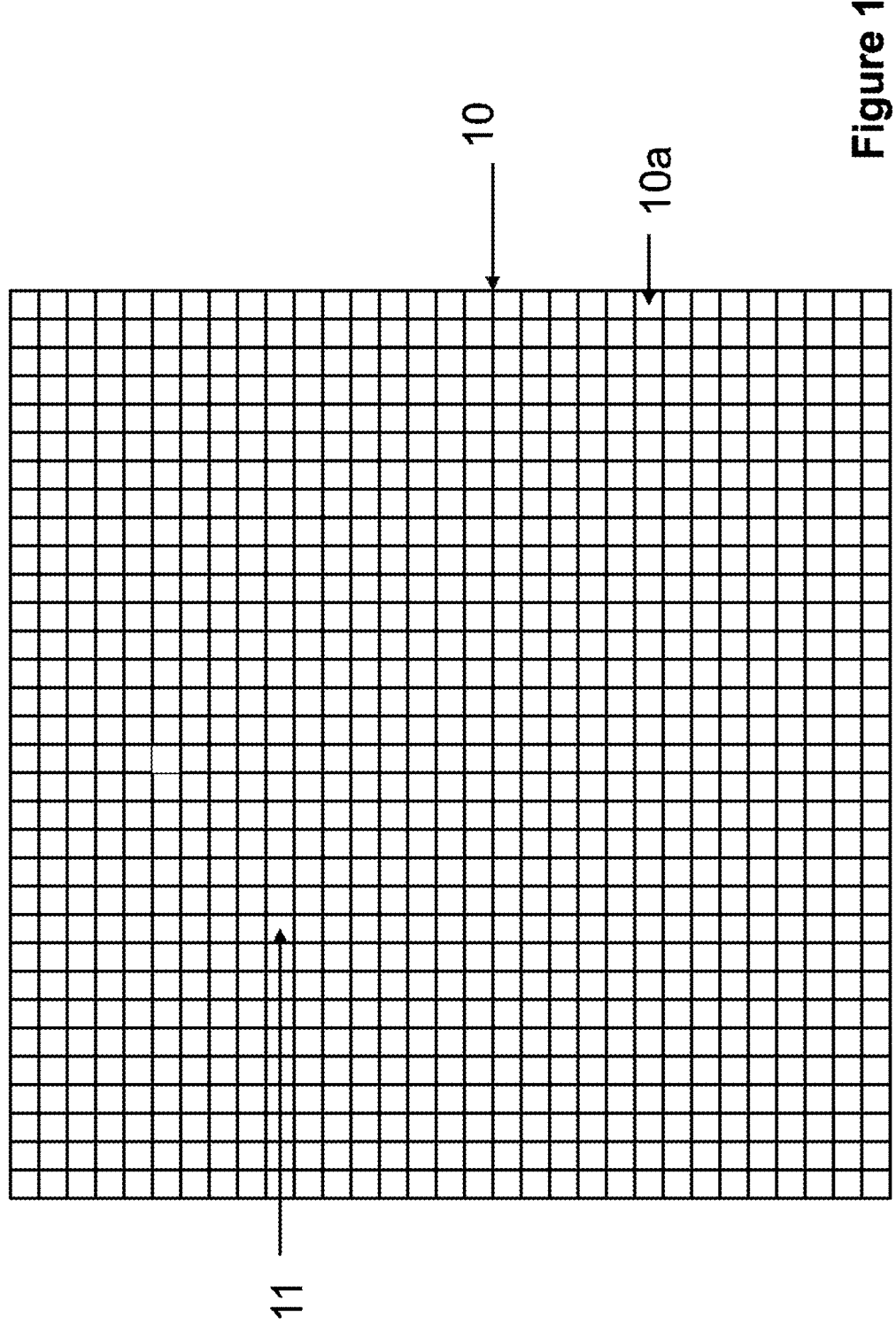
FIG. 1 shows a display panel comprising a pre-patterned image.

The first aspect of the present invention is directed to a display panel comprising a pre-patterned image. FIG. 1 is a top view of a display panel (10) comprising microcells (10a), on which a pre-patterned image "8" (11) appears. The display panel therefore has a patterned area (11) and a background area (i.e., area outside of the patterned area).

Figure 2:
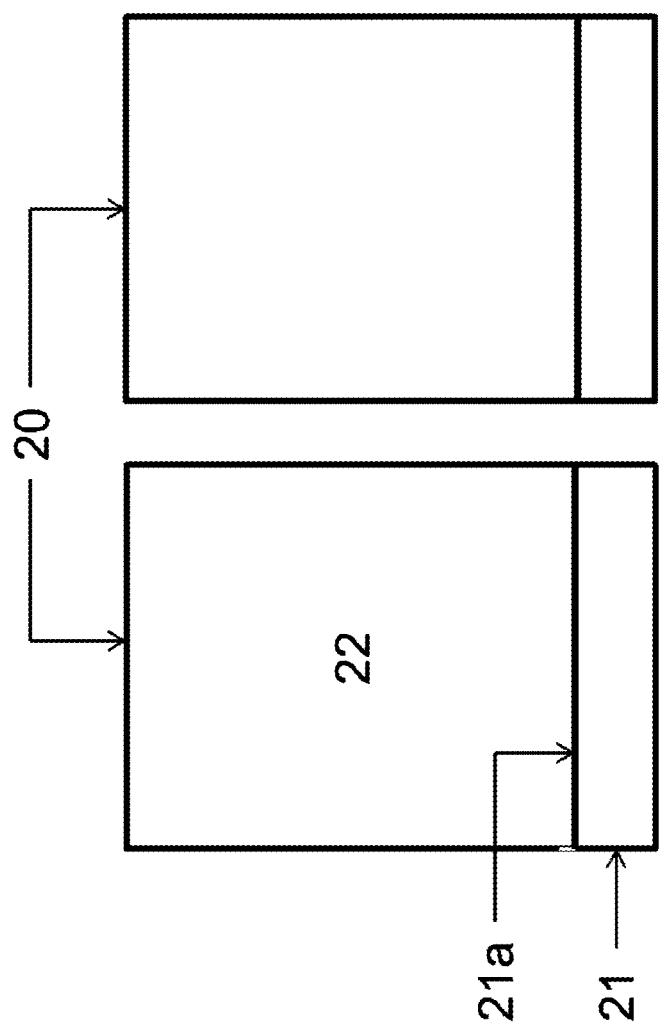
FIG. 2 is a cross-sectional view of microcells.

FIG. 2 is a cross-sectional view of microcells (20). Each microcell has a bottom (21) and the microcells are filled with a display fluid (22). The inner surface or top surface (21a) of the bottom is in direct contact with the display fluid.

In one embodiment, the term "microcell" may be a cup-like micro-container as those described in U.S. Pat. No. 6,930,818. It includes MICROCUP®.

FIG. 3 is a cross-section view of microcells in a display panel of the present invention. The panel has a first area and a second area. In the context of this application, the term "first area" refers to an area in which the microcells (30b) have substantially the same bottom thickness and the term "second area" refers to an area in which the microcells (30a) have bottoms which are thicker than those in the microcells in the first area. The term "substantially the same" refers to variation in thickness being within manufacturing tolerance, for example, ±5%.

The microcells (30a) in the second area have an added thickness "t", which may be in the range of 0.001 micron to 9/10 of the depth ("d") of the microcells in the first area (where the depths of the microcells are substantially uniform), preferably in the range of 0.001 micron to ½ of the depth of the microcells in the first area. In other words, the bottom thickness of the microcells in the second area is in the range of 0.001 micron to 9/10 of the depth of the microcells in the first area, preferably in the range of 0.001 micron to ½ of the depth of the microcells in the first area, more than the bottom thickness of the microcells in the first area.

The second area may be a patterned area while the first area is a background area, or vice versa.

The added bottom thicknesses in individual microcells in the second area do not have to be the same. Some of them may be thicker than the others.

The display panel of the present invention may be prepared by a variety of methods.

FIGS. 4A and 4B illustrate an embossing process as described in U.S. Pat. Nos. 6,831,770 and 6,930,818. As shown, an embossable composition (40) is first coated over a substrate layer (41). The substrate layer is on a nip roller (42). A male mold (43) is pressed onto the embossable composition to form microcells (44). The embossable composition for forming the microcells may be hardened during or after the male mold is released. In this method, the microcells have substantially uniform bottom thickness.

There may be optionally an electrode layer attached to the substrate layer (41). When the electrode layer is present, the embossable composition is coated on the electrode layer side. In this scenario, the electrode layer would be one of the two layers sandwiching the display panel in the final product.

When the electrode layer is not present in the process, the substrate layer attached to the resulting display panel may be removed after the embossing process, and replaced with an electrode or another substrate layer.

Figure 5:
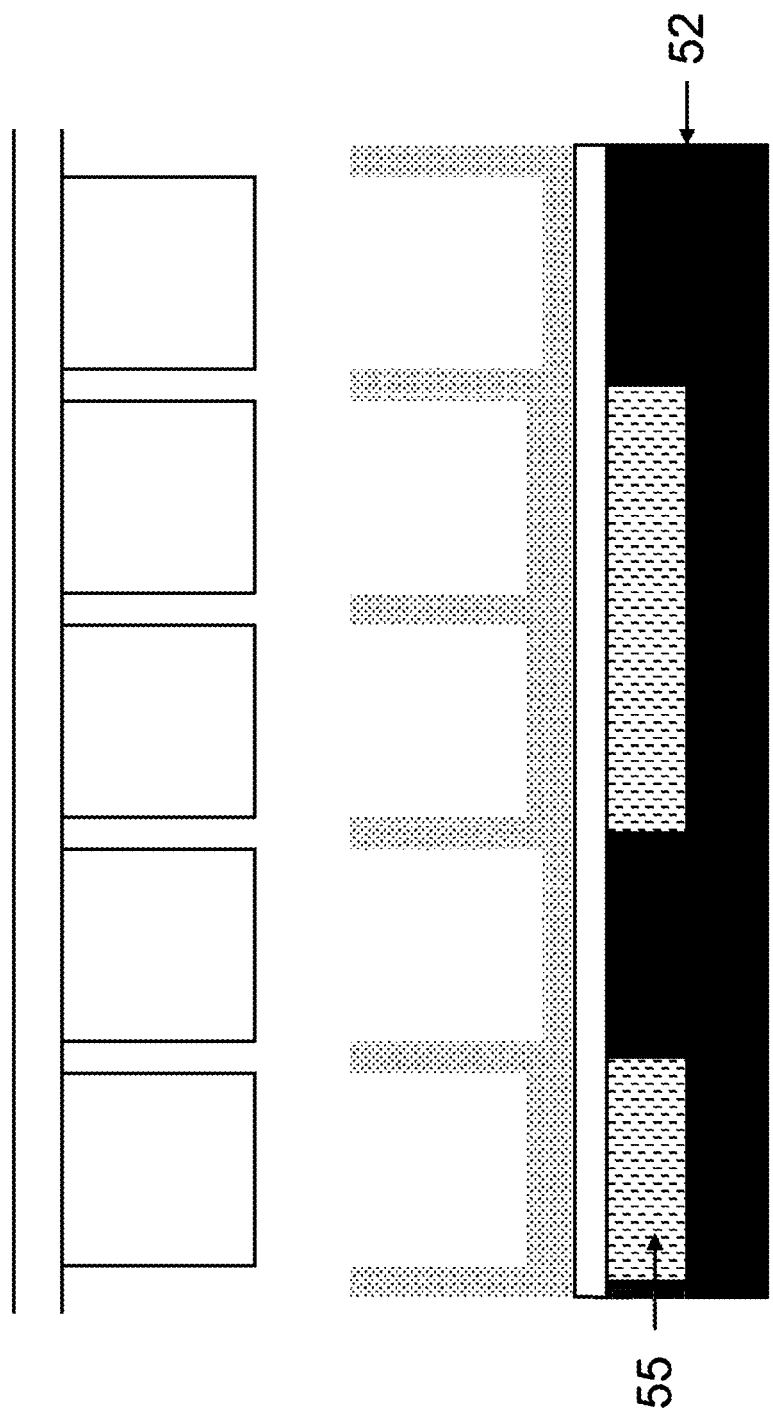
FIG. 5 illustrates a method for preparing a display panel of the present invention.

In order to prepare a display panel with pre-patterned images, the method illustrated in FIGS. 4A and 4B is modified by carving out areas (55) on the nip roller (52) (see FIG. 5) to form a pattern which may be a "positive" image or "negative" image of the intended pattern for the display panel.

In the embossing process, the pressure from the male mold exerted on the embossable composition in the carved-out areas is less than the pressure exerted on the embossable composition from the male mold in other areas. As a result, the bottoms of the microcells in the resulting display panel corresponding to the carved-out areas are thicker. The degree of the added thickness may be adjusted by altering the depth of the carved-out areas on the nip roller. A deeper carved out area on the nip roller would result in a thicker bottom of a microcell in the corresponding area.

The term "positive image", referred to above, indicates that the carved-out pattern on the nip roller is the same as the intended pattern for the display panel. In this case, the display panel formed would have a patterned area in which the microcells have thicker bottoms.

The term "negative image", referred to above, indicates that the carved-out pattern corresponds to an area excluding the intended pattern for the display panel. In this case, the display panel formed would have a background area in which the microcells have thicker bottoms.

The surface of a nip roller is curved. However it is drawn as a straight line in FIGS. 4 and 5, for illustration purpose only.

The added thicknesses of the microcells do not have to be the same, which can be achieved by the method as described. In other words, variation in the depth of the carved-out areas on the nip roller will result in variation in the bottom thickness of the microcells.

Suitable embossable compositions for forming the microcells are disclosed previously. U.S. Pat. Nos. 6,831,770 and 6,930,818 describe that a suitable composition for forming microcells may comprise a thermoplastic, thermoset, or a precursor thereof. Examples of thermoplastic or thermoset precursor may include multifunctional acrylate or methacrylate, multifunctional vinylether, multifunctional epoxide and oligomers or polymers thereof. A crosslinkable oligomer imparting flexibility, such as urethane acrylate or polyester acrylate, may also be added to improve the flexure resistance of the embossed microcells.

U.S. Pat. No. 7,880,958 describes a further embossable composition for microcells which may comprise a polar oligomeric or polymeric material. Such a polar oligomeric or polymeric material may be selected from the group consisting of oligomers or polymers having at least one of the groups, such as nitro ($-NO_2$), hydroxyl ($-OH$), carboxyl ($-COO$), alkoxy ($-OR$ wherein R is an alkyl group), halo (e.g., fluoro, chloro, bromo or iodo), cyano ($-CN$), sulfonate ($-SO_3$) and the like. The glass transition temperature of the polar polymer material is preferably below about 100° C. and more preferably below about 60° C. Specific examples of suitable polar oligomeric or polymeric materials may include, but are not limited to, polyhydroxy functionalized polyester acrylates (such as BDE 1025, Bomar Specialties Co, Winsted, Conn.) or alkoxylated acrylates, such as ethoxylated nonyl phenol acrylate (e.g., SR504, Sartomer Company), ethoxylated trimethylolpropane triacrylate (e.g., SR9035, Sartomer Company) or ethoxylated pentaerythritol tetraacrylate (e.g., SR494, from Sartomer Company).

U.S. patent application Ser. No. 13/686,778 discloses another type of embossable composition for forming microcells. The composition comprises (a) at least one difunctional UV curable component, (b) at least one photoinitiator, and (c) at least one mold release agent. Suitable difunctional components may have a molecular weight higher than about 200. Difunctional acrylates are preferred and difunctional acrylates having a urethane or ethoxylated backbone are particularly preferred. More specifically, suitable difunctional components may include, but are not limited to, diethylene glycol diacrylate (e.g., SR230 from Sartomer), triethylene glycol diacrylate (e.g., SR272 from Sartomer), tetraethylene glycol diacrylate (e.g., SR268 from Sartomer), polyethylene glycol diacrylate (e.g., SR295, SR344 or SR610 from Sartomer), polyethylene glycol dimethacrylate (e.g., SR603, SR644, SR252 or SR740 from Sartomer), ethoxylated bisphenol A diacrylate (e.g., CD9038, SR349, SR601 or SR602 from Sartomer), ethoxylated bisphenol A dimethacrylate (e.g., CD540, CD542, SR101, SR150, SR348, SR480 or SR541 from Sartomer), and urethane diacrylate (e.g., CN959, CN961, CN964, CN965, CN980 or CN981 from Sartomer; Ebecryl 230, Ebecryl 270, Ebecryl 8402, Ebecryl 8804, Ebecryl 8807 or Ebecryl 8808 from Cytec). Suitable photoinitiators may include, but are not limited to, bis-acyl-phosphine oxide, 2-benzyl-2-(dimethylamino)-1-[4-(4-morpholinyl)phenyl]-1-butanone, 2,4,6-trimethylbenzoyl diphenyl phosphine oxide, 2-isopropyl-9H-thioxanthen-9-one, 4-benzoyl-4'-methyldiphenylsulphide and 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propane-1-one, 2,2-dimethoxy-1,2-diphenylethan-1-one or 2-methyl-1[4-(methylthio)phenyl]-2-morpholinopropan-1-one. Suitable mold release agents may include, but are not limited to, organomodified silicone copolymers such as silicone acrylates (e.g., Ebercryl 1360 or Ebercyl 350 from Cytec), silicone polyethers (e.g., Silwet 7200, Silwet 7210, Silwet 7220, Silwet 7230, Silwet 7500, Silwet 7600 or Silwet 7607 from Momentive). The composition may further optionally comprise one or more of the following components, a co-initiator, monofunctional UV curable component, multifunctional UV curable component or stabilizer.

The contents of all of the patents/patent applications referred to above are incorporated herein by reference in their entirety.

Figure 6:
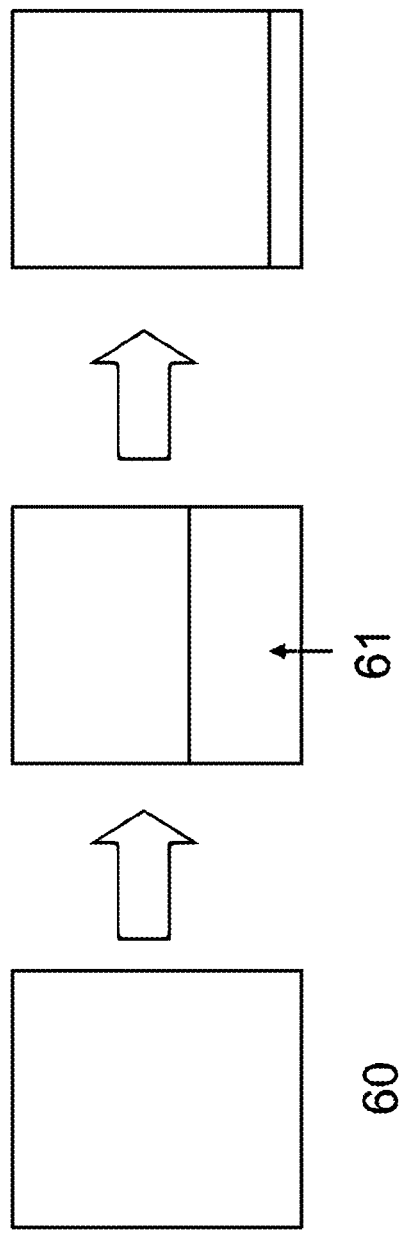
FIG. 6 illustrates an alternative method for preparing a display panel of the present invention.

Alternatively, the display panel of the present invention may be prepared as shown in FIG. 6. In this case, the microcells may be first prepared according to the method of FIGS. 4A and 4B. After the embossable composition is hardened and microcells (60) are formed, a chemical composition (61) is filled into the microcells in a pre-determined area (which may correspond to the patterned area or the background area on the display panel). The chemical composition contains a solid material dissolved or dispersed in a solvent that can be easily removed.

The filling of the chemical composition in the pre-determined area may be accomplished by methods, such as inkjet printing or screen printing.

The solid material may be a curable material, such as any of those described above for the embossing composition. There may be an optional curing step, after the solvent is removed, if the solid material is a curable material. The curing may be accomplished by known conventional methods, such as, thermal cure or radiation cure.

The solid material may also be a material which does not need curing, such as polyurethane, poly(ethylene oxide), polystyrene, acrylate polymers [such as poly(methyl acrylate) and poly(butyl acrylate)] or methacrylate polymers [such as poly(methyl methacrylate) and poly(ethyl methacrylate)].

It is noted that the solid material in the chemical composition does not have to be the same as the embossable composition for forming the microcells.

Examples of suitable solvent for this method may include, but are not limited to, methyl ethyl ketone, acetone or isopropyl alcohol. After the chemical composition (61) is filled into the microcells in the pre-determined area, the solvent in the chemical composition is removed by evaporation or boiling.

Once the solvent is removed, the remaining solid material in the chemical composition should provide good adhesion to the bottom of the microcells and also does not inter-react with the display fluid to be filled in the microcells.

The added thickness in the microcells is determined by the solid content in the chemical composition. In other words, the added thickness in the microcells may be determined by the concentration of the chemical composition. Usually, a concentration in the range of 0.01% to 90% by weight, preferably in the range of 0.01% to 50% by weight, is suitable.

The microcells may also be filled with chemical compositions with different concentrations, resulting in different bottom thicknesses.

In either one of methods described above, after the microcells are formed, a display fluid is filled into the microcells. The display fluid may be an electrophoretic fluid which comprises charged particles dispersed in a solvent or solvent mixture.

Figure 7:
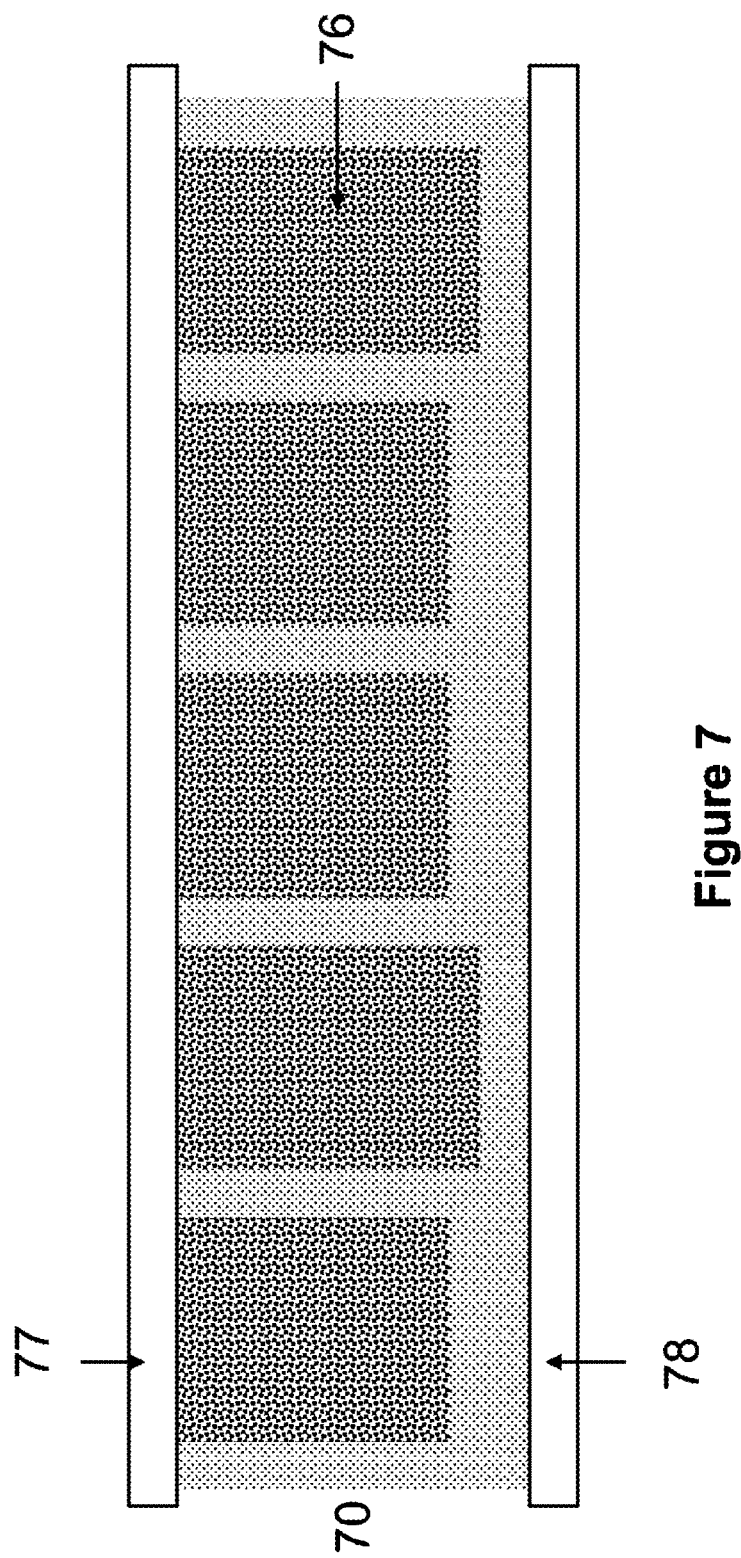
FIG. 7 shows a display panel of the present invention sandwiched between two electrode layers.

With an electrophoretic fluid (76) filled in, a display panel (70) with pre-determined images is sandwiched between two electrode layers (77 and 78), as shown in FIG. 7.

Traditionally, an electrophoretic fluid may have one type of charged pigment particles dispersed in a solvent or solvent mixture of a contrasting color. In this case, when a voltage potential difference is imposed between the two electrode plates sandwiching the display panel, the charged particles migrate by attraction to the plate of polarity opposite to that of the particles. Thus, the color showing at the transparent plate may be either the color of the solvent or the color of the pigment particles. Reversal of plate polarity will cause the charged particles to migrate back to the opposite plate, thereby reversing the color. Alternatively, an electrophoretic fluid may have two types of charged particles of contrasting colors and carrying opposite charges, and the two types of pigment particles are dispersed in a clear solvent or solvent mixture. In this case, when a voltage potential difference is imposed between the two electrode plates sandwiching the display panel, the two types of pigment particles would move to the opposite ends (top or bottom). Thus one of the colors of the two types of the pigment particles would be seen at the viewing side. In another alternative, charged particles of additional colors are added to an electrophoretic fluid for forming a highlight or multicolor display device. All of these options are suitable for the display panel of the present invention.

Figure 8:
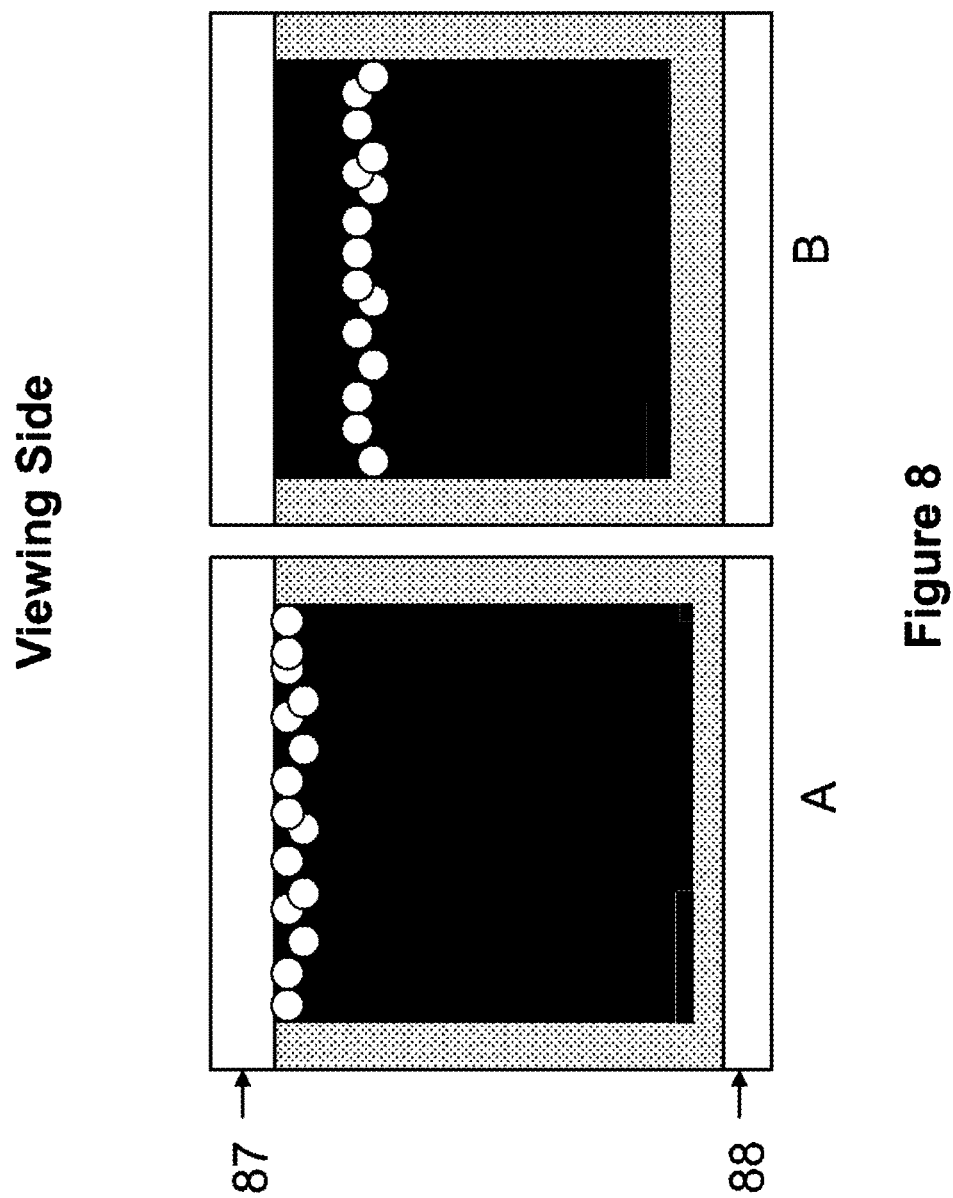
FIG. 8 shows how different levels of color intensity may be achieved by a display panel of the present invention.
Figure 9:
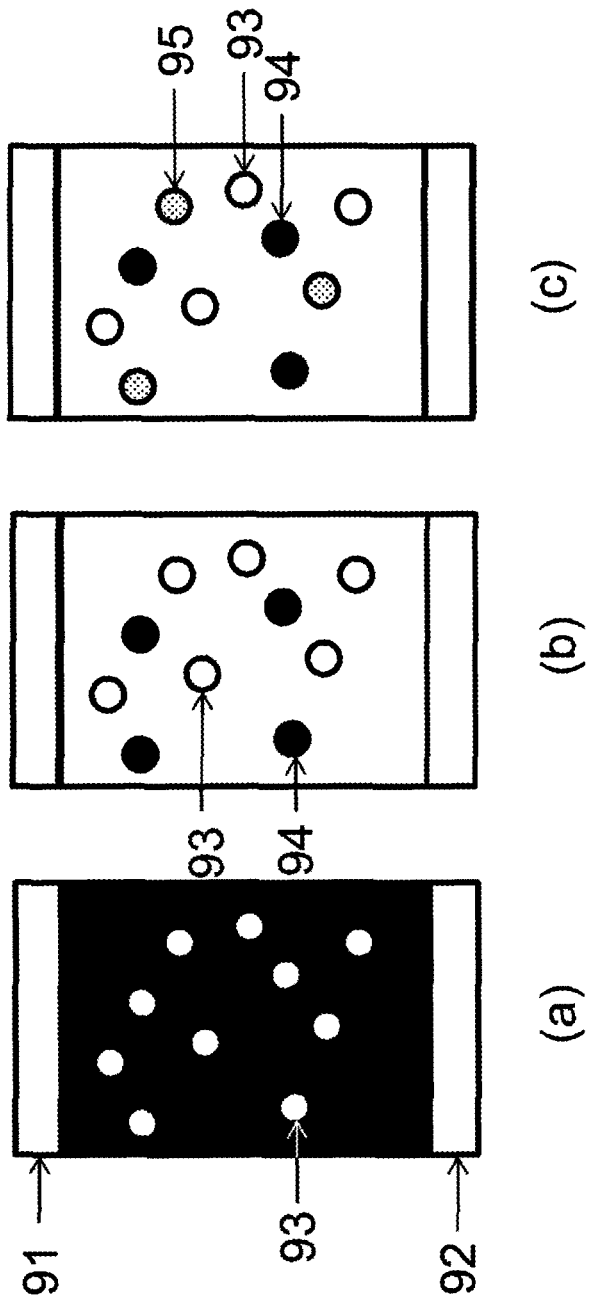
FIG. 9 shows alternative designs of the present invention.

Because of the different bottom thicknesses, the charged particles in microcells in one area would respond to the electric field created between the two electrode layers differently from the charged particles in microcells in another area, thus causing different color intensity levels to be displayed. FIG. 8 illustrates one example of this phenomenon. The white particles in microcell A (in one area) respond to the electric field created between electrode layers 87 and 88, and move to be near or at the electrode 87, and as a result, a white color is seen at the viewing side. In microcell B (in another area), because of the thicker bottom, the white particles sense a weaker electric field and as a result, a grey color is displayed.

Since in the area represented by microcell B, the microcells may have different bottom thicknesses, different levels of color intensity (i.e., greyscale) are therefore possible.

While FIG. 8 only demonstrates a design with only one type of charged particles, the phenomenon exhibited is applicable to electrophoretic fluids having any number of types of charged particles.

In one embodiment of the present invention, both electrode layers are non-patterned conductive layers such as indium tin oxide, copper or aluminum. In this case, when a voltage potential difference is imposed on the two electrode layers, an area in which the microcells have different levels of bottom thickness from those in other areas, will be shown in a color state which has different intensity from that of the other areas. This design is particularly suitable for signage displays having fixed images, such as bar code, anti-counterfeiting labels, direction signage or shelf labels.

In another embodiment, one of the electrode layers is a common electrode while the other electrode layer is a TFT (thin film transistor) matrix driving system or segmented backplane driving system. In this case, the entire display panel may switch from one image to another image while one area remains to be distinguishable visually from another area. This embodiment of the present invention is particularly suitable as a watermark and the watermark does not interfere with the switching of the images.

In a further embodiment, the inner surface of the microcells may be treated to modify its chemical functionality, morphology, microstructure, charge characteristics, surface tension or optical density.

For example, the surface may be treated with electron donating or proton accepting probe molecules or precursors thereof, including but are not limited to, ammonia, amines, imines, pyridines, ureas, thioureas, urethanes, pyrrolidones, imidazoles, ethers, thioethers, ketones, acrylates and acrylamides. Alternatively, the surface may be treated with electron accepting or proton donating probe molecules or precursors thereof, including but are not limited to, oxygen, carboxylic compounds, hydroxy containing compounds, acrylamides, silanols or organometallic compounds comprising an electron deficient center.

Another option of surface treatment involves modification of the chemical functionality of the microcell surface by plasma or corona treatment to induce interaction between the charged pigment particles and the surface. One specific example is to modify the surface by plasma treatment using probe molecules having a functional group which is capable of forming a hydrogen bonding or acid-base reaction with a functional group on the surface of the dispersed particles. The hydrogen bonding may be formed from a proton donor or electron acceptor on the microcell surface and a proton acceptor or electron donor on the particles, or vice versa.

Further alternatively, the surface may be modified with plasma treatment to form a steric stabilization or protective colloid layer on the cell surface.

All of the surface treatment methods mentioned above and other options are described in U.S. Pat. No. 6,870,662, the content of which is incorporated herein by reference in its entirety.

It is also noted that the surface treatment of the microcells may be applied to all microcells or to only selected microcells, depending on the needs.

The subject matter presented herein can also be adopted to construct an active molecule delivery system whereby active molecules can be released on demand and/or a variety of different active molecules can be delivered from the same system and/or different concentrations of active molecules can be delivered from the same system. This subject matter is well-suited for delivering pharmaceuticals to patients transdermally, however the concepts presented herein may be used to deliver active ingredients, generally. For example, the present subject matter can deliver tranquilizing agents to a horse during transport. The active delivery system includes a plurality of microcells, wherein the microcells are filled with a medium including active molecules. The microcells include an opening, and the opening is spanned by a porous diffusion layer. The microcell arrays may be loaded with different active ingredients, thereby providing a mechanism to deliver different, or complimentary, active ingredients on demand.

In addition to more conventional applications, such as transdermal delivery of pharmaceutical compounds, the active molecule delivery system may be the basis for delivering agricultural nutrients. For example, the microcell arrays can be fabricated into large sheets that can be used in conjunction with hydroponic growing systems, or the microcell arrays can be integrated into hydrogel film farming. See, for example, Mebiol, Inc. (Kanagawa, Japan). The active molecule delivery systems can also be incorporated into the structural walls of smart packing. Such delivery systems makes it possible to have long term release of antioxidants into a package containing fresh vegetables. This "smart" packaging will dramatically improve the shelf life of certain foods, and it will only require the amount of antioxidant necessary to maintain freshness until the package is opened. Thus, the same packaging can be used for food that is distributed locally, across the country, or around the globe.

The present subject matter may also provide for a system for simple and low cost delivery of "cocktails" of active molecules on demand. Such a delivery system may be used, for example, as an emergency delivery system for a person undergoing an allergic reaction. The system may include epinephrine, as well as antihistamines. The device can be applied and then triggered to cause the actives to be quickly passed through the skin. The system may be particularly effective as a back-up system for small children who may be exposed to life-threatening allergens while on a field trip, etc. A parent can affix the delivery system to the child with instructions to activate the device in the event of, e.g., a bee sting. Because the device is relatively simple, compliance with proper delivery protocols will be greater than, e.g., an epipen.

Figure 10:
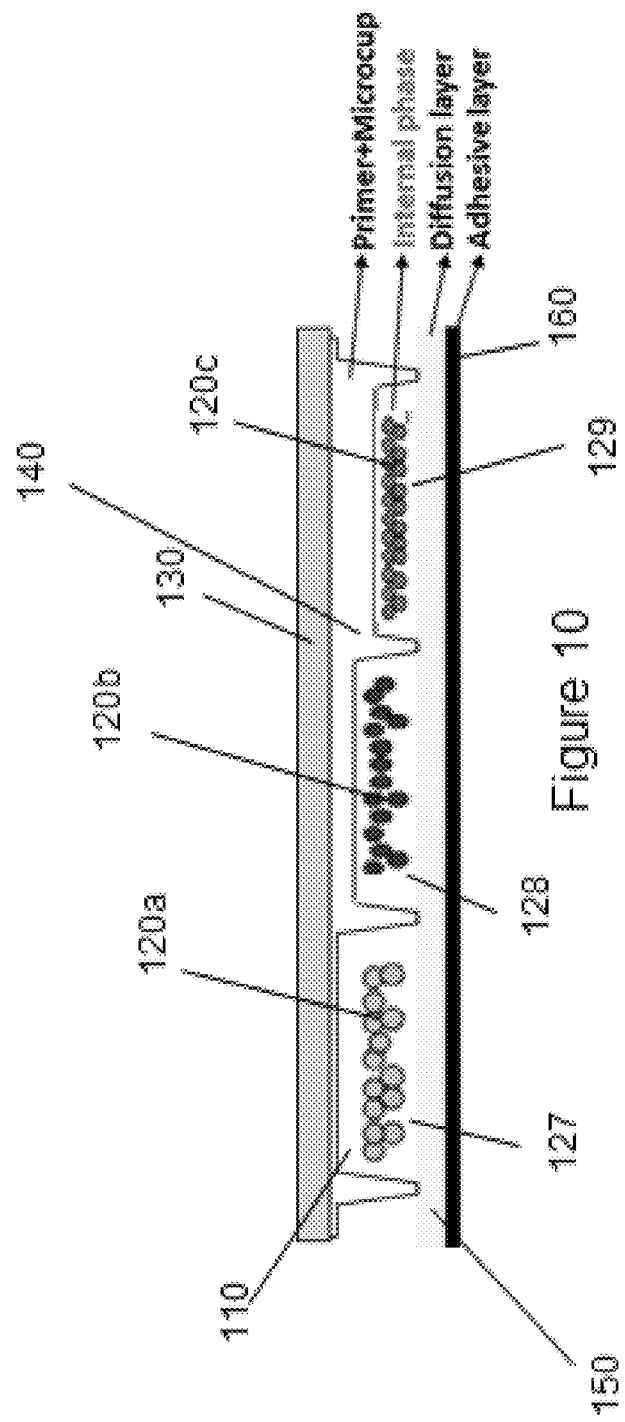
FIG. 10 illustrates an embodiment of an active molecule delivery system including a plurality of microcells including a porous diffusion layer wherein different microcells have different volumes.

An overview of an active molecule delivery system is shown in FIG. 10. The system includes a plurality of microcells 110, where each microcell may have different bottom thickness and can include a medium (a.k.a. internal phase), that includes an active molecule 120$a$/$b$/$c$. As shown in FIG. 10, a first microcell may include a first active 120$a$, while a second microcell includes a second active 120$b$, while a third microcell includes a third active 120$c$. Each microcell 110 is part of an array that is formed from a polymer matrix, which is described in more detail below. The active molecule delivery system will typically include a backing barrier 130 to provide structural support and protection against moisture ingress and physical interactions. The microcells are defined by walls 140 that are at least 1 μm high, although they can be much higher depending upon the desired depth of the microcell. The microcells may be arranged as squares, a honeycomb, circles, etc. The microcell 110 will have an opening that is spanned by a porous diffusion layer 150, which may be constructed from a variety of natural or non-natural polymers, such as acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. Often the system will additionally include an adhesive layer 160 that is also porous to the active molecule. The adhesive layer 160 assists in keeping the active molecule delivery system adjacent to the surface. Using picoliter injection with inkjet or other fluidic systems, individual microcells can be filled to enable a variety of different actives to be included in an active molecule delivery system.

Also also shown in FIG. 10, the depth of different microcells 127, 128, 129 is varied by increasing the amount of polymer at the base of the microcell. This is easily accomplished by using a mold with the desired depth and the embossing technique described below. In other embodiments, the width of a microcell can be larger or smaller depending upon the volume of solution including an active that is desired to be contained within a given microcell.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, materials, compositions, processes, process step or steps, to the objective, spirit and scope of the present invention. All such modifications are intended to be within the scope of the claims appended hereto.

What is claimed is:

1. An active molecule delivery system comprising a plurality of microcells, wherein: each of the microcells has an opening and a bottom, the active delivery system has a first area and a second area, the microcells in the first area have substantially the same bottom thickness, and the microcells in the second area have thicker bottom than the microcells in the first area, and the openings of the microcells is spanned by a porous diffusion layer.

2. The active molecule delivery system of claim 1, wherein the microcells in the second area have a bottom thickness which is 0.001 micron to 9/10 of the depth of the microcells in the first area, more than the bottom thickness of the microcells in the first area.

3. The active molecule delivery system of claim 1, wherein the microcells in the second area have a bottom thickness which is 0.001 micron to ½ of the depth of the microcells in the first area, more than the bottom thickness of the microcells in the first area.

4. The active molecule delivery system of claim 1, wherein the bottom thicknesses of the microcells in the second area are not the same.

5. A method for preparing an active molecule delivery system of claim 1, comprising:
   a) providing microcells;
   b) filling the microcells in a pre-determined area, with a chemical composition containing a solid material dissolved or dispersed in a solvent;
   c) removing the solvent; and
   d) optionally curing the chemical composition after removal of the solvent.

6. The method of claim 5, wherein the solvent is methyl ethyl ketone, acetone, or isopropyl alcohol.

7. The method of claim 5, wherein the microcells are filled with different concentrations of the solid material in the chemical compositions.

8. The method of claim 7, wherein the concentrations of the solid material in the chemical compositions are in the range of 0.01% to 90% by weight.

9. The method of claim 7, wherein the concentrations of the solid material in the chemical compositions are in the range of 0.01% to 50% by weight.

10. The method of claim 5, wherein the chemical composition is not the same as a composition from which the microcells are formed.

11. The method of claim 5, wherein the chemical composition is the same as a composition from which the microcells are formed.

12. The active molecule delivery system of claim 1, wherein the openings of the microcells in the first area and the second area have substantial the same surface area.

* * * * *